(12) United States Patent
Lindenberg et al.

(10) Patent No.: US 6,649,344 B1
(45) Date of Patent: Nov. 18, 2003

(54) ASSAY TO INDICATE THE PRESENCE OF NON-FERTILIZABLE OVA

(75) Inventors: Svend Lindenberg, Skodsborg (DK); Anne Lis Mikkelsen, Frederiksberg (DK)

(73) Assignee: Medi-Cult A/S, Jyllinge (DK)

( * ) Notice: Subject to any disclaimer, the term of this patent is extended or adjusted under 35 U.S.C. 154(b) by 0 days.

(21) Appl. No.: 09/720,472

(22) PCT Filed: Jun. 22, 1999

(86) PCT No.: PCT/DK99/00344

§ 371 (c)(1),
(2), (4) Date: Mar. 3, 2001

(87) PCT Pub. No.: WO99/67644

PCT Pub. Date: Dec. 29, 1999

(30) Foreign Application Priority Data

Jun. 22, 1998  (DK) ........................................ 1998 00885

(51) Int. Cl.$^7$ ............................................. G01N 33/533
(52) U.S. Cl. ........................... 435/6; 435/7.1; 435/7.92; 435/7.94; 435/510; 436/501; 436/806; 436/811
(58) Field of Search ........................... 435/7.1, 6, 7.92, 435/7.94, 510; 436/501, 806, 811

(56) References Cited

FOREIGN PATENT DOCUMENTS

| EP | 0833160 | 1/1998 |
|---|---|---|
| WO | WO9110445 | 7/1991 |
| WO | WO9532431 | 11/1995 |
| WO | WO9730175 | 8/1997 |

OTHER PUBLICATIONS

Carson et al. Successful Fertilization of Human Oocytes in Vitro: Concentration of Estradiol, progesterone and androstenedione. Journal of Clinical Endocrinology and Metabolism. vol. 55, No. 6, 1982, pp798–800.*
Suchanek et al. European Journal of Obstetrics and Gynecology and Reproduction Biology 56 (1994) 121–127.*
Souza et al. Endocrinology vol. 138 No. 12, 1997.*
DeLauzon et al. Journal of Clinical Endocrinology and Metabolism (Apr. 1996) 81(4) 1401–5.*
Ebrahim et al. Journal of Assisted Reproduction and Genetics 1993 Feb 10(2) 130–6.*
Muasher et al. Fertility and Sterility. Aug. 1988 50(2) 298–307.*
Groome et al. Endocrionolgy (Dec. 1997) 138 (12) 5333–40.*
Groome, Np et al., "Measurement of Dimeric . . . ," Journal of Clinical Endocrinology and Metabolism, vol. 81, No. 4, pp. 1401–1405.
Cha, Ky et al., "Successful in vitro maturation . . . ," Fertility and Sterility Abstracts O–044, vol. 66, No. suppl Month, pp.S23.
Hall Je et al., "Inhibin A and Inhibin B . . . ," Human Reproduction, vol. 14, No. 2, Feb. 1999, pp. 409–415.
Medline, Washington DC USA; Abstract No. 99199761, Abstract XP002119135 & J. E. Hall et al.: "Inhibin A and Inhibin B reflect ovarian function in assisted reproduction, but are less useful at predicting outcome." Human Reproduction, vol. 14, No. 2, I Feb. 1999 (Feb. 1, 1999), pp. 409–415, Boston MA USA.
Russell Jb et al., "Unstimulated immature oocyte . . . ," Fertility and Sterility, vol. 67, No. 4, Apr. 1997, pp. 616–620.
Barnes Fl et al., "Production of embryos . . . ," Fertility and Sterility, vol. 65, No. 6, Jun. 1996, pp. 1151–1156.
Wynn P et al., "Randomized study of oocytes . . . ," Human Reproduction, vol. 12, Abstract Book 1, Jun. 1997, pp. 13–14.
Flood J et al., "Ooplasmic transfusion: prophase . . . ," Fertility and Sterility, vol. 53, No. 6, Jun. 19, pp. 1049–1054.
Cha Ky et al., "Pregnancy after in vitro fertilization . . . ," Fertility and Sterility, vol. 55, No. 1, Jan. 1991, pp. 109–113.
Trounson A et al., "In vitro maturation . . . ," Fertility and Sterility, vol. 62, No. 2, Aug. 1994, pp. 353–362.

* cited by examiner

Primary Examiner—Christopher L. Chin
Assistant Examiner—Pensee T. Do
(74) Attorney, Agent, or Firm—Birch, Stewart, Kolasch & Birch, LLP

(57) ABSTRACT

The present invention relates to an assay for at least one predictive marker in a sample from a mammal wherein a specific reaction for at least one predictive marker indicates when non-fertilizable ova capable of in vitro maturation (IVM) and subsequent in vitro fertilization (IVF) are present in the mammal. This is particularly useful in the determination of when non-fertilizable ova, if aspirated, after in vitro maturation to MF-II will be capable of fertilization and pregnancy after implantation into the female mammal. The assay is based on a sample selected from the group consisting of body secrete, sputum, blood, urine, uterus secretes and cells.

19 Claims, No Drawings

ASSAY TO INDICATE THE PRESENCE OF NON-FERTILIZABLE OVA

This application is the national phase under 35 U.S.C. §371 of PCT International Application No. PCT/DK99/00344 which has an International filing date of Jun. 22, 1999, which designated the United States of America.

BACKGROUND OF THE INVENTION

The normal ovulating woman will recruit approx. 300 immature oocytes (ova) for each menstrual cycle. Normally, during a process of apoptosis all but one oocyte will die before ovulation. Conventional in vitro fertilisation (IVF), treatment for special cases of severe male and female infertility, is based on retrieval of mature human ova followed by fertilisation of the mature oocytes with spermatozoa. The recruitment of human mature oocytes is accomplished by several complicated forms of hormone treatment regimens, often with discomfort or risk for the women involved. These hormone treatment regimens will especially become a problem in the future, as IVF is increasingly offered to perfectly normal women in these programs due to their husbands' poor sperm quality. Furthermore, this type of treatment will normally provide a pregnancy rate of 20% per started cycle.

Because of the risk, discomfort and cost of the hormonal stimulation several other approaches have been tried during the years. In animals in vitro maturation (IVM) has become an efficient method for producing oocytes for IVF, but until now recorded success rates for clinical human IVM have been low (Cha, Trounson, Barnes, Russel). One of the most simple ways to avoid hormonal stimulation has been not to stimulate with hormones at all. This treatment regimen, however, has only provided a limited numbers of pregnancies and the calculated pregnancy rate is never beyond 5% per started cycle.

SUMMARY OF THE INVENTION

The present invention relates to the ability of a test system to predict the timing and development of specific healthy, activated prophase ova to develop further in vitro up to MF-II without exogenous hormonal treatment of the woman, and hereby avoid the degeneration of the majority of the ova, even though the woman is not treated with hormones. In contrast to all other previous hormonal assays always focusing on later stages of ova development, usually ova in the MF-II stage, the measurements aim at the timing of aspiration of non-fertilisable ova, which can mature in vitro to be fertilised. By this method pregnancy rates of more than 15% are achieved.

DETAILED DISCLOSURE OF THE INVENTION

Scientific Background

The nuclear development of the ova are arrested in the diplotene phase as germinal vesicles. This is referred to as the dicytate stage. This stage is characterised by highly diffuse chromosomes, the DNA of which has little affinity for such nuclear strains as Feulgen's reagent. The chromosomes of ova in the dicytate stage bear lateral projections in the form of branches and loops which actively replicate ribonucleic acid (RNA). They closely resemble the "Lampbrush" chromosomes, which are found almost universally in eggs of lower vertebrates and some invertebrates. The RNA may act as the messenger directing protein synthesis within the ova itself. Circumstantial evidence from studies of ova in frogs and toads suggest that some of the RNA may act as the early organiser of mammalian development. Whatever the outcome of the additional studies required to elucidate these complex problems, the dicytate stage should clearly not be referred to as a resting phase, since the oocytes show a high degree of metabolic and synthetic activity at a time when the follicular envelope consist of only a few flattened epithelia cells.

Human oocyte/folicular development is a controlled mechanism both in time and biological processes. 99% of all ova are arrested in the meiotic prophase (that is the dicytate stage) even before birth. From this pool a couple of hundred ova are selected and activated every month (the menstrual cycle) for further development that is resumption of the meiosis though germinal vesicle breakdown (GVB) and Metaphase I (MF-I) to Metaphase II (MF-II) and growth of the follicle.

The reproductive state of the human female is cyclic with a complex interaction between the hypothalamus, anterior pituitary and the ovaries eventually leading to the process of ovulation. The cycle is repeated with an average period of 28–30 days (range 25–35 days). The first phase, menstruation, last 4–5 days. The first day of a cycle is the first day of the first phase, that is the first day of menstrual bleeding. The second follicular phase of the ovary corresponds to the proliferative phase of the endometrium and lasts 10–16 days (i.e. highly variable). Then follows an ovulatory phase (36 hours) and finally a luteal phase which corresponds to the secretory phase of the endometrium and is usually constant at 14 days. Three components critical to the understanding of the menstrual cycle:

1. hypothalamic GnRH control of FSH/LH release,
2. ovarian follicular development to ovulation and subsequent corpus luteum formation and
3. the feedback control of FSH/LH secretion by ovarian hormones.

During the second half of the reproductive cycle, the corpus luteum develops and secretes both oestrogen and progesterone. Oestrogen continues to promote the proliferative activity in the endometrium. Progesterone on the other hand causes the endometrial glands to become distended with secretory products which include glycogen (important for the developing embryo should implantation occur). Endometrial blood flow increases and the spiral arteries become coiled and twisted. The second half of the cycle is called the luteal phase (ovaries) or the secretory phase (uterus). If implantation does not occur then the corpus luteum regresses, there is a rapid fall in the secretion of oestrogen and progesterone, the endometrium undergoes shrinkage due to extracellular fluid loss, the spiral arteries constrict, the endometrial blood flow decreases with cell death and destruction of blood vessels. These chances eventually lead to a phase of menstrual bleeding where all but the basal layer of the endometrium is lost. The first day of the menstrual bleeding is, for practical reasons the first day of the menstrual cyclus.

Ova maturation is the final stage of ova development that prepares for fertilisation and embryo development. It can be divided into two general processes: nuclear maturation and cytoplasmic maturation. Nuclear maturation is defined as the resumption of meiosis and progression to MF-II while cytoplasmic maturation is defined as the extragenomic changes that prepare the egg for activation, pronuclear formation, and early embryogenesis.

The follicle surrounding the ova in the dicytate stage comprises a single layer of flattened granulosa cells. The signs of further development of the ova and follicle involves further multiplication in the number of granulosa cells and also the passage of fluid into spaces between the granulosa cells. As the quantity of fluid increases, the cavities that it occupies increases in size and become confluent to form an antrum. The follicle is now said to be of the Graafian type. With the further expansion of the antrum, the ova occupies a position at one side of the follicle and is surrounded by two or more layers of granulosa cells. The innermost layer of these cells becomes columnar in the shape and constitutes the corona radiata which, as the innermost part of the cumulus oophorus, persists around the egg for a period after ovulation.

The nuclear maturation proceeds in parallel with the follicular development Thus, GVB and MF-I ova are observed during the formation of the antrum that is in the antral and pre-antral follicle. By the time the antrum is fully developed the meiotic division is completed and the first polar body extrusion is seen.

A few hundred ova reach this stage during each menstrual cycle. However, due to presently unexplained factors, the majority of these enter atresia, wherein the ova undergo an apoptotic process and die. The dissolution of the innermost part of the granulosa cells whilst the egg is still in the follicle, or precociously after its departure, is a sure sign that degenerative changes are occurring that will result in the death of the ova. Only a few, normally only 1, will proceed the development.

Technical Background of IVF

If the woman receives FSH, more than one follicle will proceed developmentally to MF-II avoiding atresia.

By MF-II is understood an oocyte with 1 polar body, and expanded cumulus complex and which has finally gone through a germinal vesicle break-down. These oocytes are readily recognised by a routine technician normally handling oocytes for IVF. MF-II ova are the type of ova which are prepared and able to be fertilised by the sperm cell. At no earlier stage in the development of the ova is this presently possible.

Conventional in vitro fertilisation (IVF) treatments aim at gaining as many as possible of the ova in MF-II. This has been obtained by exogenous hormonal treatment of the woman, including follicular stimulation hormone (FSH). rFSH, or urin derived FSH, is administered in the dose of 100 to 250 IU/day. Often this treatment is continued for 8–10 days. Futher treatment with GNRH agonists such as Buserelin daily are added to the treatment. By this treatment the degeneration of most of these activated ova is avoided. This type of hormonal treatment always includes the risk of hyper-stimulation syndrome and other side effects such as the increased risk of ovarian cancer, nausea, discomfort, oedema, pain, allergic reaction to the medication, depression and weight gain, all of which are hard to justify specifically if the woman is healthy and the reason for the IVF treatment is due to a severe male infertility problem. Thus, at the moment, more than 30% of all IVF cycles in the world are initiated with heavy medication of the women although the problem is a male factor.

In order to obtain healthy MF-II ova, the hormonal treatment of the woman has been supplemented with monitoration of serum hormone levels of Estradiol, FSH, LH, progesterone, PP14, and/or PP12. The timing of the aspiration of healthy MF-II ova has further been aided by ultrasound scanning of the follicular development. All of these clinical tests have been devised to increase the healthiness and number of recruitable MF-II ova.

IVM

IVM preferably starts with immature or not fully matured gametes. In the woman the ova will be recognised as oocytes with a tight cumulus mass, no polar bodies or Germinal vesicles visible. These ova are readily recognised by a person involved in routine IVF-treatments as being immature ova.

If no hormones are administrated only one oocyte will mature as seen in normal ovulating women. By releasing the immature oocytes from the ovary prior to initiation of the apoptotic processes wherein the ova enter atresia, and subsequently mature the ova further in vitro, the women can avoid the risk and discomfort associated with hormonal treatment and still a sufficient number of mature Metaphase II (MF-II) ova will be available for subsequent in vitro fertilisation.

It has been possible to produce oocytes whose nuclear maturation has progressed to MF-II, but which are incompetent to complete preimplantation development. The importance of cytoplasmic control over developmental competence has been described in the immature monkey oocyte. Using micromanipulation, ooplasm was removed from MF-II oocytes and injected into prophase I oocytes. Monkeys receiving the oocytes with cytoplasmic transfusion had a sevenfold increase in pregnancy rate compared to oocytes without ooplasm injection (Flood).

Up to this date IVM protocols published have either used a fixed day in the menstrual cycle, calculated from the previous ovulation or the onset of menses, or just used a convenient day prior to final development of the antral follicles. This has gained pregnancy rates from 0%–10%.

The Invention

The present invention relates to the finding that the measurement of specific signalling hormones will be indicative of the appropriate timing of ova aspiration for an IVM procedure. This measurement being indicative of the timing of aspiration of ova will optimise the number of ova specifically capable of further maturation in vitro, fertilisation and further development. The identification of specific signalling hormones as predictive markers for when non-fertilisable ova capable of in vitro maturation and subsequent fertilisation, cleavage, implantation and pregnancy are present in the mammal greatly increases the rate of success in IVM cycles.

A non-fertilisable ova is in this patent application an immature ova (=oocyte) that upon contact with a mature sperm cell will not complete the meiotic division and accept the genetic material from the sperm cell and form a fertilised cell. It is presently anticipated that the endocrine and intra-ovarian regulation of ova maturation will leave the ova with a precise, but complex composition of substances with specific concentrations or concentration ratios, such that the non-fertilisable ova after in vitro maturation to MF-II will be capable of fertilisation, subsequent cleavage and then pregnancy after implantation into the female mammal.

One aspect of the invention thus relates to an assay for the presence or quantity of at least one predictive marker in a sample from a mammal wherein a specific determination of the presence or quantity of the at least one predictive marker indicates when non-fertilisable ova capable of in vitro maturation and subsequent fertilisation are present in the mammal.

The assay for the at least one predictive marker is based on a sample from a female mammal. In one embodiment of the invention the sample is a sample selected from the group consisting of e.g. Body secrete, body fluid, cellular nutrients, follicle content, sputum, blood, urine, faeces, uterus or vaginal secretes and components, menstruation products, epitelia and epitelia derived components, skin components, and dead or living cells. A person skilled in the art will readily understand how each of these samples are obtained.

In one embodiment of the present invention, the sample originates from a mammal, such as a pet, e.g. cat, dog, or guinea pig; or a zoo animal e.g. a primate. In another embodiment of the invention, the mammal is a laboratory animals such as a rat, or a mouse. In further preferred embodiments, the mammal is part of the industry, preferably a farm animal such as cattle, a horse, pig, mink, goat, or sheep. In the presently most preferred embodiment, the mammal is a human being.

In one aspect of the invention, the female mammal is tested prior to ova aspiration. Possibly more than one test is performed. Either an absolute cut off level or a relative measure such as a plateau, an increase or a decrease of the before mentioned selective marker can predict the timing of the ova aspiration for IVM.

In this context, a predictive marker should be understood as any substance that will change concentration, colour, structure, confirmation, and/or reaction pattern in a biological, physical or chemical test. It is to be understood that a lot of potential predictive markers exist. In one embodiment of the invention the assay is an assay, wherein the at least one predictive marker is a hormone selected from the group consisting of gonadotrophins (such as FSH, LH, prolactin, and HCG), thyoidea hormones (such as TSH, T3, and T4), and steroid hormones (such as sex hormones: Estradiol, estrogens, estratriol, progesterone, and testosterone; androgenes: cortisone or cortisole). In another embodiment of the invention the assay is an assay, wherein the at least one predictive marker is a small peptide hormone (such as GIP or VIP). In another embodiment of the invention the assay is an assay, wherein the at least one predictive marker is a peptide hormone (such as PP12, PP14, an inhibin: inhibin A or inhibin B: activin, or $\alpha 1$ or $\alpha 2$ globulins). In another embodiment of the invention the assay is an assay, wherein the at least one predictive marker is a lipid selected from the group consisting of Meiosis Activating Sterols (MAS) lipids and prostaglandines. In another embodiment of the invention, the assay is an assay, wherein the at least one predictive marker is a nucleic acid selected from the group consisting of DNA fragments, mRNA, and tRNA. In another embodiment of the invention the assay is an assay, wherein the at least one predictive marker is a marker selected from the group consisting of LFN1, LFN2, LFN3, glycoconjugates, carbohydrates, cellular nutrients, integrins such as integrin 1, and carbohydrate epitopes. In another embodiment of the invention the assay is an assay, wherein the at least one predictive marker is an intra- or intercellular messenger such as cAMP. In yet another embodiment of the present invention the assay is an assay wherein the at least one predictive marker is an enzyme, such as phosphodiesterase or an inhibitor of phosphodiesterase.

Due to the high complexity of the interaction between and in-between proteins, hormones, lipids, nucleic acids, intercellular messengers, and enzymes, it is presently anticipated that the timing of the aspiration of non-fertilisable ova shall be dependent on combinations of cut off levels of certain predictive markers and/or relative measurements on one or more predictive markers, i.e. relative measurements of the same marker where the samples have been taken at different times, or relative measurements of two or more markers present in a sample at the same time.

The assay comprises at least one predictive marker. That is two predictive markers such as three, four, five or six predictive markers.

It is more than likely that the predictive value of the assay will be markedly increase if the evaluation of two or more predictive markers is combined.

Based on the description in examples 1 and 2 on how the correlation between the two predictive markers Inhibin A and Estradiol correlate to the outcome of the IVM cycle, the person skilled in the art will be able to determine such correlations between other predictive markers. In one embodiment, there is a significant correlation between the chance of pregnancy in that cycle and the relative increase, or relative decrease, in the concentration of the predictive marker subject to investigation in the sample from day 1, day 2, day 3, day 4, day 5, day 6, day 7, day 8, or even day 9 prior to the day of ova aspiration. In another embodiment, there is a significant correlation between the chance of pregnancy in that cycle and the absolute increase, the absolute decrease, or the plateau in the concentration of the predictive marker subject to investigation in the sample from day 1, day 2, day 3, day 4, day 5, day 6, day 7, day 8, or even day 9 prior to the day of ova aspiration. In yet another embodiment, there is a significant correlation between the concentration of the predictive marker subject to investigation in the sample on day 1, day 2, day 3, day 4, day 5, day 6, day 7, day 8, or even day 9 and the chance of pregnancy in that cycle. In one aspect of this embodiment, the significant correlation between the concentration of the predictive marker subject to investigation in the sample and the chance of pregnancy in that cycle is reduced to a binary correlation, such that a cut-off level is set, and the chance of pregnancy in that cycle is correlated to whether the concentration of the predictive marker subject to investigation is more or less than the cut-off level.

In one embodiment of the invention the pregnancy rate in a study of IVM-cycles wherein the time for ova aspiration has been set by an assay as described in the present invention, is more than 10%, such as more than 13%, 15%, 18%, 20%, 21%, 22%, 23%, 24%, 25%, 26%, 27%, 28%, 29%, 30%, 31%, 32%, 33%, 34%, 35% or even more than 40%.

In a presently preferred embodiment of the present invention two predictive markers are chosen. That is Inhibin A and Estradiol. As illustrated in examples 1 and 2 an increase in Estradiol and Inhibin A predicts success of the IVM-cycle.

It will sometimes be observed that the increase in Estradiol is seen prior to the increase in Inhibin A. In that case, the concentration of Estradiol might fall, or reach a plateau, by the time the increase in Inhibin A is observed. In this case it is still considered that an increase in Estradiol has been reached such that the chance for success is high, due to the fact that the increase in Inhibin A is the major factor. This is especially the case, when FSH priming is performed (see example 3).

In a presently most preferred embodiment of the present invention, the assay comprises three specific reactions and results for two selective markers. The first specific reaction is a measurement of the concentration of Inhibin A of less than 10 pg/ml in a blood sample on day 3 of the menstrual cycle. The second specific reaction and result is an increase in the concentration of Inhibin A of more than 80% from day 3 to the day of ova aspiration. The third specific reaction and result is an increase in the concentration of Estradiol of more than 87% from day 3 to the day of ova aspiration. Thus in one aspect of the embodiment, the woman will have a blood test drawn on day 3 of the menstrual cycle and the concentrations of Inhibin A and Estradiol in the blood sample are determined. If the concentration of Inhibin A is less than 10 pg/ml in said blood sample, this cycle will not be an IVM-cycle. However, if the concentration of Inhibin A is more than or equal to 10 pg/ml in said blood sample a new blood sample will be withdrawn on day 4, 5, 6, 7, 8, 9, 10, 11, 12, 13, 14, 15 and 16 unless the second specific and the third specific reaction have been observed. If the second specific and/or the third specific reaction are observed, the day of the observation should be the day, where ova are aspirated. It is contemplated, based on the results from example 2, that IVM cycles wherein the time for ova aspiration have met these three specific reactions will have pregnancy rates of more than 12%, such as more than 16%, 22%, 25%, 26% or even more than 28%.

As will be appreciated by the person skilled in the art, measurements of predictive markers in mammalian samples are routine measures. In one aspect of the invention, the assay is prepared in such a way that the specific reaction can be compared and compiled without the assistance of doctors or advanced medical equipment. However, as will be understood by the person skilled in the art, quite a few of the predictive markers can presently not be measured without expensive equipment making it necessary to transfer the sample to a laboratory setting, where the result of the assay will guide the timing of ova aspiration in the mammal.

Due to the complexity of the concentrations, relative increases, relative decreases, absolute increases, absolute decreases, plateau's and cut off values, one aspect of the invention is a scheme to be filled out during the cause of the menstrual cycle wherein IVM-treatment is contemplated. In one embodiment the scheme comprises columns for each day in the menstrual cycle and rows for each of the predictive markers such that each cell can be filled out as the measurements of the predictive markers are obtained. Automated, semi-automated, and guided manual calculations of the alterations in the predictive markers will ease interpreting the results of the specific reactions.

Ultrasound Guidance

In one embodiment of the invention, the assay for predictive markers is used as a first selection criteria. If this criteria is fulfilled the woman will be subjected to ultrasonic measurements of the uterus and ovaries. If the evaluation of the ultrasonic measurements determines:

a large number of antral follicles, the size of the leading follicle is about 10 mm, the cohort of follicles is uniform, the endometrial thickness is more than about 3 mm, and beginning trilaminaer structures of the endometrial lining the likelihood of having found the right time for successful ova aspiration, in vitro maturation to MF-II, fertilisation, implantation and pregnancy is very high.

In a presently preferred embodiment of the present invention, the ova is derived from a female human being having an ovarian follicle with a diameter of 8–12 mm. The advantage of such small follicles is that they are present in substantial numbers at this time in the menstrual cycle without prior severe hormonally treatment, they can bee seen by ultrasound, and an ultrasonically guided transvaginal puncture of the follicles is possible to perform in order to retrieve the oocytes.

It will be understood by the person skilled in the art that other sizes of ova should be aspirated from other mammals.

In one embodiment of the invention, the general knowledge of the women's menstrual cycle is incorporated in the timing of the aspiration of ova. Thus, usually the aspiration is performed between day 6 and 17, that is usually between day 9 and 11.

Thus, in one embodiment of the present invention, a method to determine the timing of ova aspiration comprises the following steps:

a) assay at least one predictive marker in a sample from a mammal;

by the time the result of the specific reaction in the assay in step a) predicts the presence of non-fertilisable ova capable of in vitro maturation and subsequent fertilisation in the mammal b) evaluate the time relative to the first day of the menstrual bleeding;

if day is between day 6 and day 17 of the menstrual cycle then c) evaluate an ultrasound picture of the ovaries of the mammal;

if the size of the follicles is between 8 mm and 12 mm and the cohort of follicles is uniform, then d) evaluate an ultrasound picture of the uterus of the mammal;

if the endometrial thickness is more than about 3 mm and beginning trilaminaer structures of the endometrial lining are observed, the time for ova aspiration is right. However, if any of the above mentioned steps fail, the cycle is probably not suitable for IVM, and the aspiration of ova should be postponed until next cycle, where the method is repeated.

The ability of IVM oocytes to complete meiosis and to become developmentally competent may be enhanced by FSH priming prior to oocyte aspiration. In human IVM a short FSH stimulation doubles the number of oocytes recovered per patient as well as increases the proportion of oocytes that attain MF-II after 48 hours. In one embodiment of the present method, the woman is treated on days 3, and/or 4, and/or 5 in the menstrual cycle with hormones such as FSH followed by a discontinuation of the treatment. In example 3, an increased maturation rate and cleavage rate was observed in the FSH priming group with a delay between the last injection and the aspiration compared to the FSH priming without a delay. In the FSH priming group with a delay between the last injection and the aspiration, an increased maturation rate was observed compared to unstimulated oocytes, but the cleavage rate of the matured MF-II oocytes was not affected. It was high in both groups. An early apoptotic phase or an artificial plateau phase in the follicular growth may mimic the final preovulatory follicular maturation in terms of developmental competence. In this way an artificial plateau or fall of the Estradiol level is obtained causing an apoptotic process in the ovary leading to the above mentioned signalling into the immature oocyte. Such a fall in Estradiol level is expected around day 10 in the menstruation cycle. Retrieval of oocytes in women without hormonal stimulation should preferably be done on day 10 in the menstruation cycle, as that day statistically is associated with numerous oocytes in a prophase.

In one aspect of the invention the woman will benefit from an initial treatment on days 3, 4, and 5 in the menstrual cycle with a hormone such as FSH followed by a discontinuation of treatment. In this treatment regimen, the blood level of Estradiol in the woman might be monitored with the object of selecting maturating oocytes, indirectly measured by none growing (growth pause) follicles. Early apoptotic oocytes destined for becoming apoptotic are characterised in that they are easily detached from the ovary during the puncture of the follicles and they have a compact cumulus mass. Then by the time of a plateau or fall in Estradiol level is observed, the retrieval of oocytes is performed. An observed plateau or fall in Estradiol concentration is due to a prior increase in the Estradiol concentration between day 3 of the menstrual cycle and the day of ova aspiration. In one embodiment the time for ova aspiration is the time of an increase in Estradiol concentraton, that is before the plateau or fall in Estradiol concentration. In a further preferred embodiment, the monitoration of Estradiol concentration is further supplemented with a monitoration of the Inhibin A concentration.

Thus, one embodiment of the present invention is a kit comprising the suitable FSH medication and an assay as described above. Optionally, the kit further comprises means to obtain the sample or samples for the assay.

References

Flood J, Chillik C F, van Uem J F H M, Iritani A, Hodgen G D. Ooplasmatic transfusion: prophase germianl vesicle oocytes made developmentally competent by microinjection of methase II egg cytoplasma. Fertil Steril 1990;53:1049–54.

Cha K Y, Koo J J, Ko J J, Choi D H, Han S Y, Yoon T K. Pregnancy after in vitro fertilization of human follicular oocytes collected from nonstimulated cycles, their culture in vitro and their transfer in a donor oocyte program. Fertil Steril 1991;55:109–13.

Russell J B, Knezevich K M, Fabian K, Dickson J A: Unstimulated immature oocyte retrieval: early versus midfollicular endometrial priming. Fertil Steril 1997;67:616–20.

Bames F L, Kausche A K, Tiglias J, Wood C, Wilton L, Trounson A. Production of embryos from in vitro-matured primary oocytes. Fertil Steril 1996;65:1151–6.

Trounson A, Wood C, Kaunsche A. In vitro maturation and the fertilization and developmental competance of oocytes recovered from untreated polycystic ovarian patients. Fertil Steril 1994;62:353–62.

Cha K Y, Chung H M, Han S Y, Yoon T K, Oum K B, Chung M K. Successful in vitro maturation, fertilization and pregnancy by using immature follicular oocytes collected from unstimulated polycystic ovarian syndrome patients. Fertil Steril Abstract O-044; 1996:Supl.S23.

Wynn, P. Picton H. M. Krapez, J., et al. (1998). Randomized study of oocytes matured after collection from unstimulated or mildly stimulated patients. *Hum. Reprod*, 13, 3132–3138.

Groome, N. P., Illingwowrth, P. J. and O'Brien, M. et al. (1996) Measurement of Dimeric Inhibin B throughout the Human Menstrual cycle. *J. Clin. Endocrin. Metab.*, 81,1401–1405.

It is to be understood that the figures and examples described below are illustrative of embodiments of the present invention, and the invention is not intended to be so limited.

EXAMPLES

A total of 83 regular cycling women referred for IVF/ICSI because of male factor and/or tubal disease were included in the study. The study was approved by the local ethical committee. All women participated in the study after written consent.

Hormone profiles (gonadotrophins, Inhibin A, Inhibin B, Estradiol and progesteron) were monitored. The hormone profiles were determined by RIA (Immuno 1, Bayer) except the profiles of Inhibin A and Inhibin B, which was determined by the method described by Groome (1996).

Immature ova collection was performed the day after a follicle of 10 mm could be detected by ultrasound. We used an aspiration needle from Cook Ltd described by Carl Wood. The aspiration pressure was reduced to 100 mmHg, on the assumption that the immature cumulus or egg may be more susceptible to mechanical injury, or the needle in a small follicle may directly damage the egg if the egg is sucked forcefully from a small volume of fluid into the end of the needle.

The follicles were punctured. After aspiration the needle was flushed with Earles Balanced Salt solution with Hepes and bicabonate buffers plus heparin (100 IU/ml) as described by Trounson et al.

The follicular aspirates were transferred in tubes to the laboratory and washed on an embryo filter with a pore size of 70 $\mu$m. Erythrocytes and other small cells were washed through the filter and oocytes and larger fragments of cells were collected in Petri culture dishes. The immature oocytes were identified and graded based on the presence or absence of cumulus cells as either completely multilayered, sparse or nude.

Oocytes were matured in tissue culture medium 199 (TCM 199; Sigma) or BBEM (Medicult, Denmark) supplemented with Sodiumpyruvate 0.3 mM, rec-FSH 0.075 IU/ml (Gonal-F; Serono), hCG 0.05 IU/ml (Profasi; Serono), and albumin 1%. Later the medium was supplemented with Estradiol 1 $\mu$g/ml and an increased concentration of HSA (5%) or serum from the patient (10%) instead of albumin.

Oocytes were denuded with hyaluronidase (IVF Science, Sweden) and mechanical pipetting. Motile sperm were prepared by Purespern™ (Cryos, Denmark) gradient separation or by swim-up. For ICSI denuded oocytes were placed individually into 5 $\mu$L drops of sperm prep medium (Medicult, Denmark) and 2 $\mu$L of sperm suspension was placed into a 10 $\mu$L drop of PVP (IVF Science, Sweden). All MF-II oocytes were inseminated by ICSI and then placed into 10 $\mu$L drops of BBEM and cultured in 5% $CO_2$ and humidified air at 37° C. Approximately 10–20 h after insemination oocytes were examined at 300× for the presence of pronuclei as a measure of successful fertilization. Embryos were cultured to day 2 or 3 (day 0=day of insemination) at which time suitable embryoa (maximum of 2) were replaced into the women. Suitable embryoa are those that are cleaved.

Example 1

Analysis of Inhibin A and Estradiol in IVM-cycles

The descriptive statistics of the data from 83 treatment cycles where the relevant endocrinological parameters were available are presented in Table 1. These 83 treatment cycles resulted in 10 pregnancies.

TABLE 1

Comparison between the group of women that became pregnant and the group of women that did not become pregnant

|  | Not Pregnant Mean ± SD | Pregnant Mean ± SD | P-value T-test* |
| --- | --- | --- | --- |
| Serum Inhibin A on day 3 (pg/ml) | 9,0 ± 3,1 | 7,4 ± 0,7 | 0,1 |
| Serum Estradiol on day 3 (nmol/l) | 0,15 ± 0,08 | 0,14 ± 0,03 | 0,7 |
| Serum Inhibin A on day of OPU (pg/ml) | 16,3 ± 9,2 | 19,6 ± 6 | 0,28 |
| Increase in Inhibin A from day 3 (%) | 87 ± 93 | 164 ± 73 | 0,01 |
| Serum Estradiol on day of OPU | 0,35 ± 22 | 0,48 ± 26 | 0,1 |
| Increase in Estradiol from day 3 (%) | 157 ± 138 | 246 ± 224 | 0,08 |
| Increase in Inhibin A x increase in Estradiol (%$^2$) | 17607 ± 26753 | 49433 ± 61156 | 0,005 |

*Non-parametric test used. The data is not distributed according to the Normal distribution.

Table 1 shows that the increase in Inhibin A from day 3 is higher in cycles where pregnancies occurred, that the increase in Estradiol is not significant, and that the increase in Inhibin A multiplied with increase in Estradiol is significantly higher in cycles where pregnancies occurred.

The ability of analysis of serum Inhibin A and Estradiol alone to discriminate between productive and non-productive treatment cycles was subsequently analysed. For that purpose, various discriminators were applied, and the statistical correlation between the data and the chance of pregnancy was determined.

TABLE 2

Discriminator: Serum Inhibin A level below 10 (pg/ml) day 3

|  | Not pregnant | Pregnant | p-value* |
|---|---|---|---|
| Inhibin A below 10 on day 3 | 51 | 10 | 0,03 |
| Inhibin A 10 or higher at day 3 | 22 | 0 | |

*Fischer Exact test

TABLE 3

Discriminator: Serum Inhibin A level below 9 (pg/ml) day 3

|  | Not pregnant | Pregnant | p-value* |
|---|---|---|---|
| Inhibin A below 9 on day 3 | 43 | 9 | 0,04 |
| Inhibin A 9 or higher at day 3 | 30 | 1 | |

*Fischer Exact test

TABLE 4

Discriminator: An increase in serum Inhibin A from day 3 to day of OPU of at least 80%

|  | Not pregnant | Pregnant | p-value* |
|---|---|---|---|
| Inhibin A increased >80% | 35 | 10 | 0,001 |
| Inhibin A increased <80% | 38 | 0 | |

*Fischer Exact test

TABLE 5

Discriminator: An increase in serum Inhibin A from day 3 to day of OPU of at least 100%

|  | Not pregnant | Pregnant | p-value* |
|---|---|---|---|
| Inhibin A increased >100% | 30 | 8 | 0,02 |
| Inhibin A increased <100% | 43 | 2 | |

*Fischer Exact test

TABLE 6

Discriminator An increase in serum Estradiol from day 3 to day of OPU of more than 87%

|  | Not pregnant | Pregnant | p-value* |
|---|---|---|---|
| Estradiol increased >87% | 47 | 10 | 0,02 |
| Estradiol increased <87% | 26 | 0 | |

*Fischer Exact test

TABLE 7

Discriminator: An increase in serum Estradiol from day 3 to day of OPU of at least 100%

|  | Not pregnant | Pregnant | p-value* |
|---|---|---|---|
| Estradiol increased >100% | 41 | 9 | 0,04 |
| Estradiol increased <100% | 31 | 1 | |

*Fischer Exact test

The ability of a combination of analysis serum Inhibin A and Estradiol to discriminate between productive and non-productive treatment cycles.

TABLE 8

Discriminator: The product of the increases in serum Inhibin A and serum Estradiol from day 3 to day of OPU of at least 7500 (% x %)

|  | Not pregnant | Pregnant | p-value* |
|---|---|---|---|
| >7500 | 46 | 10 | 0,004 |
| <7500 | 37 | 0 | |

*Fischer Exact test

TABLE 9

Discriminator: Increase in serum Estradiol from day 3 to day of OPU of at least 87% in the group with an increase in serum Inhibin A of at least 80%

|  | Not pregnant | Pregnant | p-value* |
|---|---|---|---|
| Inhibin A and Estradiol increased more than 85 and 87% | 38 | 10 | 0,2 |
| Inhibin A increased with 80% and Estradiol increased less than 87% | 7 | 0 | |

*Fischer Exact test

TABLE 10

Discriminator: Increase in serum Estradiol from day 3 to day of OPU of more than 87% in the group with no increase in Inhibin A from day3 to day of OPU

|  | Not pregnant | Pregnant | p-value* |
|---|---|---|---|
| Estradiol increased more than 87% and Inhibin A increased more than 80% | 38 | 10 | 0,03 |
| Estradiol increased more than 87% and Inhibin A increased less than 80% | 19 | 0 | |

*Fischer Exact test

TABLE 11

The effect of no increase in Inhibin A

|  | Not pregnant | Pregnant |
|---|---|---|
| Increase in Estradiol less than 87% and no increase in Inhibin A 20 | 20 | 0 |
| Increase in Estradiol less than 87% and increase in Inhibin A above 80% | 7 | 0 |

TABLE 12

The effect of no increase in Estradiol

| | Not pregnant | Pregnant |
|---|---|---|
| Increase in Inhibin A less than 80% and no increase in Estradiol | 20 | 0 |
| Increase in Inhibin A less than 80% and increase in Estradiol above 87% | 19 | 0 |

The data presented above illustrates that the level of serum Inhibin A is a strong predictor of success in IVM-cycles. These data show that no pregnancies occurred in cycles where the level of Inhibin A was above 10 pg/ml at day 3 of the menstrual cycle (Table 2). Furthermore, only on pregnancy occurred in the group with Inhibin A above 9 pg/ml at day 3 of the menstrual cycle (Table 3).

Not only the absolute level of Inhibin A on day 3 is predictive for the success in the IVM-cycle, but the rise of serum Inhibin A from day 3 to the day of ova recovery (OPU) is also. Thus, a productive cycle is strongly correlated to a rise of serum Inhibin A from Day 3 to day of OPU of at least 80% (Table 4 and Table 5).

The data regarding Estradiol show that a productive cycle is correlated to a rise in serum Estradiol of at least 87% from Day 3 to day of OPU (Table 6 and Table 7).

The concomitant rise of serum Inhibin A and Estradiol seems to be an even better predictor for IVM success. A combination of a rise in Inhibin A and Estradiol from day 3 to day of OPU is a very good predictor of a productive cycle (Table 8, Table 9, and Table 10). Also, the prediction will tell the lack of success as no pregnancies occurred in cycles without an increase of Inhibin A above 80% from day 3 to day of OPU (Table 11), and no pregnancies occurred in cycles with an increase in Inhibin A and no increase in Estradiol (Table 12).

Example 2

Use of the Inhibin A and Estradiol Parameters for Prospective Analysis of IVM-cycles The predictive effect of the parameters determined in example 1 using an analysis of Inhibin A and Estradiol to determine which cycles should proceed to ova aspiration.

TABLE 13

Effect of cancelling cycles with elevated Inhibin A at day 3

| | Not pregnant | Pregnant | Pregnancy rate (%) |
|---|---|---|---|
| All cycles | 83 | 10 | 12,1 |
| Cycles with Inhibin A below 10 (pg/ml) at Day 3 | 62 | 10 | 16,1 |
| Cycles with Inhibin A below 9 (pg/ml) at Day 3 | 52 | 9 | 17,3 |

TABLE 14

Effect of cancelling cycles with no rise of Inhibin A at day of OPU

| | Not pregnant | Pregnant | % |
|---|---|---|---|
| All cycles | 83 | 10 | 12,1 |
| Only cycles with rise in Inhibin A from Day 3 to Day of OPU above 80% | 45 | 10 | 22,2 |

TABLE 15

Effect of cancelling cycles with Inhibin A at 10 (pg/ml) or more at day 3 or no Inhibin A rise at day of OPU above 80%

| | Not pregnant | Pregnant | % |
|---|---|---|---|
| All cycles | 83 | 10 | 12,1 |
| Selected cycles | 40 | 10 | 25.0 |

TABLE 16

Effect of cancelling cycles with Inhibin A at 10 (pg/ml) or more at day 3 or the product of increase in Inhibin A and Estradiol from day 3 to day of OPU of less than 7500%

| | Not pregnant | Pregnant | % |
|---|---|---|---|
| All cycles | 83 | 10 | 12,1 |
| Selected cycles | 38 | 10 | 26,3* |

*Significantly different from "All cycles" (p<0,05 CHl2-test)

TABLE 17

Effect of cancelling cycles with Inhibin A at 10 (pg/ml) or more at day 3 or no rise in Inhibin A and Estradiol at day of OPU

| | Not pregnant | Pregnant | % |
|---|---|---|---|
| All cycles | 83 | 10 | 12,1 |
| Selected cycles | 35 | 10 | 28,6* |

*Significantly different from "All cycles" (p<0,05 CHl2-test)

These data indicate that cycles destined to become unproductive can be cancelled based on measurements of Inhibin A early in the treatment cycle and Inhibin A and Estradiol later in the cycle (Table 13, Table 14, Table 15, Table 16, Table 17). These measurements will greatly increase the efficiency of an IVM-cycle. The data collected so far indicate that each patient can alternate between cycles with high Inhibin A early in the cycle (no pregnancy) and cycles with low Inhibin A early in the cycle (pregnancy).

Example 3

The Impact of FSH Priming

The ability of immature oocytes to spontaneosly resume meiosis when removed from the follicle was first demonstrated by Pincus and Enzman in 1935 Human oocytes from small follicles can resume and complete meiosis in vitro, but to a lesser extent than in other mammals (Edwards, 1965). Successful maturation of unstimulated oocytes have been reported (Cha et al., 1991; Trounson et al., 1994; Bames et al., 1996; Russell et al.,1997,) and high rates of fertilization can be achieved, when these oocytes are subjected to intracytoplasmatic sperm injection (ICSI) (Russell et al., 1997), but the developmental potential has been reported to be low (Cha and Chian, 1998; Barnes et al. 1996). The IVM protocol is relatively simple with a shorter period of treatment and reduced costs compared to conventional IVF. In addition the side effects of ovarian superovulation especially hyperstimulabon syndrome is eliminated. Despite the poor pregnancy rate seen in human trials until now, the record of success in laboratory animals have been encouraging. In monkeys FSH priming has been shown to enhance nuclear and cytoplasmic maturation of oocytes in vitro (Schramm and Bavister, 1994). Increasing FSH levels within the follicle is coincident with the generation of a positive signal necessary to complete in vivo oocyte maturation in humans. (Gomez et al., 1993) and a short FSH stimulation has been shown to increase the percentage of oocytes that reach metaphase II. (Wynn et al., 1998) after in vitro maturation.

In this prospective randomised pilot study we investigated whether the developmental potential of in vitro matured immature oocytes may be improved by FSH priming before the aspiration.

Materials and Methods

Included in the study were couples referred for IVF/ICSI because of male factor and/or tubal disease. The women were at least 18 and at most 38 years of age and had normal ovulatory cycles with a mean length of between 24 and 35 days and a Body Mass Index (BMI) between 18 and 29 kg/m². Excluded were all patients with infertility caused by endocrine abnormalities such as hyperprolactinaemi, polycystic ovary syndrome and previous controlled ovarian hyperstimulation cycles in which less than three oocytes were retrieved. Further excluded were all women with elevated FSH value (>15 IU) on cycle day 3.

The study was approved by the local ethical committee. All couples participated in the study after written consent. The first experiment was a randomized prospective study including twenty patients recruited among couples scheduled for ICSI due to male factor. The women were randomly allocated to two groups. Group I (n=10 cycles) received no stimulation, Group II (n=10 cycles) received rec-FSH (Gonal-F, Serono) 150 IU/day for 3 days initiated day 3. Aspiration was performed the day after a leading follicle of 10 mm was observed at ultrasound. All the oocytes were matured in vitro for 36 hours before ICSI.

In the second experiment consecutive twelve couples were included. All the women received rec-FSH (Gonal F, Serono) priming before aspiration and 150 IU was given daily from day 3. Five patients received the same stimulation as group 2 in the first experiment with a fixed dose of 150 IU/day for 3 days and aspiration the day after a leading follicle of 10 mm was observed. The remaining seven patients continued stimulation until the leading follicle was 10 mm and aspiration was performed 72 hours later. All the oocytes were cultured for 48 hours until fertilization with ICSI.

In all patients a transvaginal ultrasound was performed on cycle day 3 and a baseline FSH, LH, Oestradiol, Inhibin A and Inhibin B was obtained. Hormone profiles were followed from day three until the day of aspiration. In the case of an ovarian cyst the cycle was cancelled. The second ultrasound examination was performed day 6–7 and the following days ultrasound was performed daily or with an interval of 2–3 days depending on the size of the follicles.

In both experiments endometrial priming consisted of 17-β-oestradiol started the day of oocyte retrieval, and the women received 2 mg orally three times per day. An endometrial thickness <6 mm at ultrasound the day of aspiration was not accepted. Two days after aspiration, treatment with intravaginal progesteron suppositories was initiated and continued until the pregnancy test. Oestrogen and Progesterone were continued if the pregnancy test was positive until 50 days gestation.

Oocyte recovery was performed transvaginally with a 17-G Cook needle with a reduced aspiration pressure as described by Trounson et al. (1994). The follicular aspirates were transferred in tubes to the laboratory and washed on an embryo filter with a pore size of 70 μm. The maturation and fertilization is described in detail by Smith et al. (1998), but in brief the oocytes were matured in tissue culture medium 199 (TCM 199; Sigma, Roedovre, Denmark) supplemented with Na purovate 0.3 mM, 1500 IU/ml penicillin G, 50 mg/ml streptomycin sulfate, oestradiol 1 μg/ml (all from Sigma), rec-FSH 0.075 IU/ml (Gonal-F; Serono), hCG 0.5 IU/ml (Profasi; Serono), and serum from the patient (10%). Serum from the patients was obtained the day of aspiration. Oocytes were cultured separately in 25 μl drops of IVM medium under paraffin oil at 37° C. in 5% $CO_2$. An oocyte was classified as having undergone germinal vesicle breakdown when the nuclear membrane was absent and was classified as a mature metaphase II (MII) oocyte when the first polar body was extruded.

Fertilization with ICSI was performed on all metaphase II oocytes. The oocytes were then placed into 10 μl droplets of IVF medium (Medicult, Copenhagen Denmark) and cultured under oil in Falcon petri dishes to day 2 after fertilization. Embryos were scored on a scale of 1–4 where types 1 and 2 (<10% fragmentation) were considered to be transferable (Deschacht et al. 1988). A maximum of two embryos were transferred. The embryo development rate was defined as the number of transferable embryos out of the total number of oocytes injected. The implantation rate was defined as the number of gestational sacs seen on ultrasound examination out of the total number of embryos replaced.

Ultrasound Measurements

Follicular diameters were measured by the same observer during transvaginal ultrasound scanning using a 7.5 Mhz transvaginal transducer (Brüel & Kjaer). The follicular diameter was calculated as the mean of the longest follicular axis and the axis perpendicular to it in the same scanning plane.

Statistical Methods

Statistically analysis were done by the Students T-test. Because none of the hormone variables displayed a normal distribution the nonparametric Mann-Whitney U-test was used to analyze statistically significant differences between unpaired data and Pratts test for paired data. Values were considered significant when p<0.05.

Results

Patients.

In experiment 1 the median age of the women was 31 years (range 28–36 years) in the group without FSH priming and 32 years (range 28–36 years) in the group that received FSH. This did not differ from the age of the women in experiment 2 (median 32 years (range 27–37 years). Other clinical characteristics including duration of infertility, cause of infertility and number of previous IVF cycles were similar in all the groups.

First Experiment: Maturation and Embryo Development.

In the first experiment including 20 women, 77 oocytes could be used for IVM, and 62 (81%) matured to MFII after 36 hours. After fertilization with ICSI, 2PN fertilization was seen in 49 (79%) and of these 45 (72%) cleaved. The embryo development rate was 40/62 (65%) and implantation rate 5/33 (15%). The clinical pregnancy rate per started cycle was 5/20 (25%). One patient had a miscarrige in the eighth gestational week, the remaining are ongoing. FSH priming did not show to have any effect on oocyte maturation, fertilization rate, cleavage rate nor embryo development (Table 18). In total five pregnancies were obtained. One has delivered a healthy boy, one has had a miscarriage in the eighth gestational week, the remaining are ongoing beyond 32 weeks of gestation.

Hormone Profiles.

There were no differences between the two groups in the levels of oestradiol, FSH, LH, inhibin A and inhibin B on day three and the day of aspiration, respectively (Table 19). In the non-stimulated group the FSH levels during follicular phase did not differ from the the values of the stimulated group, although a large inter-individual variation was observed. The level of serum oestradiol remained at the same level from day three to day 6–7 in the group without stimulation. The day of aspiration a significant increase was seen. In the stimulated group the concentration of oestradiol increased earlier (day 6–7) with a plateau phase before aspiration. No premature LH peak was observed in the two groups.

The levels of Inhibin-A showed the same pattern as the level of oestradiol with an early increase in the stimulated group and a late increase in the non-stimulated group. In the unstimulated group the level of Inhibin-B increased earlier than inhibin A. (day 6–7). At this time an increase was also observed in the stimulated group but the level was 3-fold the non-stimulated group and a significant decrease in inhibin-B was observed from day 6–7 until aspiration.

Second Experiment:

In the second experiment including 12 women, 38 oocytes could be used for IVM, and after 48 hours 27 (71%) had matured and were fertilized by ICSI. The fertilization rate and cleavage rate was 61% and 53%, respectively, and this did not differ from the fertilization rate and cleavage rate obtained in experiment 1. Fifteen embryos were transferred in 10 patients, none were cryopreserved. One pregnancy was obtained with the delivery of a healthy girl. The embryo development in this group was 56% and the implantation rate 7%. By prolongation of the stimulation period from a fixed dose of 150 IU/day for three days up to 6 days until follicles were 10 mm, we obtained an increased size of the follicles the day of aspiration and an increased level of oestradiol in serum, but the number of oocytes obtained per aspiration did not increase (Table 20).

Safety.

No hospitalization due to infection, bleeding or abdominal pain referred to as gynaecological was observed in this study. No extrauterine pregnancy was observed.

Discussion.

To our knowledge this is the first study reporting a pregnancy rate of 25% per aspiration with an implantation rate of 15% after in vitro maturation of oocytes. The immature oocytes in this study appeared to perform almost as well as those recovered after superovulation and maturation in vivo (Meldrum, et al., 1998).

The number of oocytes recovered from nonstimulated regular cycling women did not differ from the yield of oocytes recovered and matured in the study by Barnes et al (1996). Pretreatment of patients with recombinant FSH did not increase the number of oocytes recovered. Previous studies have given conflicting results. Wynn et al (1998), reported an increased number of oocytes recovered in regular menstruating women with FSH priming compared to women without FSH priming while Trounson et al (1998) did not demonstrate any difference in the number of oocytes obtained. Previous observations have suggested, that the number of recruitable follicles is fixed as early as the preceeding luteal phase (Gougeon and Testart, 1990) and a short, early FSH stimulation do not alter the number of recruitable immature oocytes. This is in accordance with the results in the present study. With increasing amount of FSH and increasing size of the follicles in experiment 2 we observed that the chance of obtaining oocytes at aspiration did not increase. This is in agreement with previous publications (Templeton et al.), where the chance of obtaining oocytes from these large follicles in the abscence of hCG was very low.

The maturation, fertilization and cleavage rates observed in the present study are consistent with the findings in previous studies, but we observed a higher pregnancy rate and a higher implantation rate indicating an improved embryo development of the oocytes. A number of factors may account for this. The embryo development of IVM oocytes may be improved by prior FSH priming. In Rhesus monkeys a short FSH priming improved the maturation and cleavage rate (Schram and Bavister, 1994). In humans, pregnancies have been obtained following the transfer of immature oocytes from stimulated cycles (Nagy et al., 1996, Liu et al., 1997; Jaroudi et al., 1997; Edirisinghe et al., 1997).

Recently Wynn et al (1998) has reported an increased maturation rate of oocytes after pretreatment with FSH. In the first experiment, however, FSH priming of the women before oocyte pick-up did not improve the maturation rate in vitro. There are two possible explanations for the difference observed: (1) the culture conditions used or (2) the timing of aspiration. The timing of fertilization and the culture conditions are important factors, and these have been discussed by Smith et al. 1999. The aspiration of oocytes was performed on a fixed day (day 7 in the menstrual cycle) in the study by Wynn et al, while the day of aspiration in the present study depended on the size of the follicles. In the stimulated group the day of aspiration was performed earlier (medium day 9) compared to the non-stimulated group (medium day 10) (Table 19), but the day of aspiration was fixed in the same way in the two groups. The size of the follicles was monitered by ultrasound and oocyte pick-up was performed the day after a leading follicle of 10 mm was demonstrated.

No fertilization of MII oocytes was performed in the study by Wynn et al (1998). In the present study FSH priming did not have any effect on fertilization rate nor cleavage rate. This is consistent with the data from Trounson et al (1998). They have reported, that treatment of natural cycling women with recombinant FSH for 3 days had no effect on the maturation rate and fertilization rate in vitro. In the present group of regular menstruating women their own FSH stimulation seemed to be sufficient to obtain oocytes that are competent to mature in vitro. We know from previous studies, that a wide interindividual difference in follicular phase FSH on day 3 and marked inter individual variation of maximum FSH concentration has been demonstrated (Schipper, et al., 1998). This inter individual variation in the levels of FSH may reflect differences in FSH threshold and differences in ovarian sensitivity to FSH and this may be one of the possible reasons for the lack of difference in maturation rate and fertilization rate although the level of FSH differed.

In the non-stimulated group we observed an increase in serum concentrations of oestradiol and inhibin A the day of aspiration and this is known to be concomitant with the selection of the dominant follicle (Schipper, et al., 1998). The concentration of inhibin-B increased earlier than inhibin A, and the level of both hormones was maintained until the day of aspiration. This is in accordance with previous studies (Schipper et al.; 1998, Groome et.al., 1996) and in accordance with our ultrasound imaging as the day of aspiration was just after the dominant follicle at 10 mm had been demonstrated. This implies, that the oocytes selected for IVM in these cases were obtained from follicles destined to go into atresia and we observed, that the embryo development of oocytes was not affected adversely by early stages of atresia. This has previously been demonstrated in cattle (Smith et al., 1996).

Production of both inhibin-A and inhibin-B is dependent on gonadotrophin (Lockwood et al., 1996) and in the gonadotropin stimulated group in the present study a three fold rise in the levels of both inhibin-A and inhibin-B was observed during stimulatin with FSH. From day 6–7 until aspiration the levels of both inhibin A and inhibin B significantly decreased and this observation is in accordance with non-growing follicles (Price et al., 1995).

The timing of aspiration and selection of oocytes for IVM is based on experience with other mammalian species (Eppig et al.; 1992; Edwards 1965 but also human oocytes appear to have a size dependant ability to resume meiosis and complete maturation (Durenzi et al., 1995). Tsuji et al., 1985 found a decreased maturation rate of oocytes from small follicles (3–4 mm) compared to oocytes from larger follicles (9–15 mm). Dubey et al (1995) also observed a decline in fertilization rates of oocytes from superovulation follicles of decreasing size. While 58% of the oocytes from folicles 10–14 mm fertilized, 74% of oocytes from follicles 22–26 mm did so. In the present study we observed that oocytes from large follicles in the second experiment with high dose gonadotropin stimulation were competent to mature and cleave (Table 20) but also oocytes from follicles at the size of 8–10 mm were develomental competent when aspiration was performed after the leading follicle was demonstrated at ultrasound. Russell et al (1998) has experienced a dramatic decrease in the rates of maturation and fertilization when immature oocytes were aspirated when the size of the dominant follicle exceeded 14 m. This indicate, there may be a critical point where the selection proces may have a negative effect on the exsisting follicles. Monitoring the diameter of the follicles may prove to be useful as a practical means of selecting oocytes competent for in vitro maturation. fo. Factors other than the size of the follicle appear to limit the efficiency of the IVM system. Priming of the endometrium is another important factor. In an immature oocyte cycle adequate endogenous oestradiol from the dominant follicle is lacking. Therefore exogenious priming is needed and one must synchronize the window of implantation with the embryo development (Russell et al., 1997) found an increased maturation rate and fertilization rate when midfollicular priming with oestradiol was initiated compared to early endometrial priming. We know from hormone replacement in recipients of donor oocytes that two day old embryos are best transferred to the endometrial cavity on the 3$^{rd}$ or 4$^{th}$ day of progesterone exposure (Rosenwaks et al. 1987). We aimed to imitate the normal priming as close as possible and initiated oestradiol the day of aspiration and supplemented with progesterone two days later. One might expect that in cycles with FSH priming the elevated concentration of oestradiol from day 6–7 might prepare the endometrium better than in nonstimulated cycles, where oestradiol increased just prior to the aspiration. We were not able to demonstrated any difference in the rate of implantations between the two groups and this is in accordance with previous studies as no correlation between follicular phase serum oestradiol concentration and implantation rate has been found (Younis et al.; 1996, Remohi et al. 1997).

These results need to be confirmed in a larger number of patients. They could lead to an attractive alternative to controlled ovarian hyperstimulation for in vitro fertilization. Besides the clinical benefits of lowering side effects, especially elimination of hyperstimulation syndrome, this treatment may reduce costs of IVF. Recently the extensive use of drugs for ovarian stimulation has been questioned by Edwards et al., 1997. Many attempts have been made to perform IVF in the natural cycle without the use of exogenous gonadotrophins. The combination of immature oocyte retrieval and IVM may enhance the success of natural cycle IVF. In IVF/ICSI because of male factor most of the women are producing their own FSH to assist the stimulation of ovarian follicles, and this may be utilized in IVM. No benefit of low dose FSH priming compared to the natural cycle on embryo development could be demonstrated in this study. However more studies are needed to elucidate this topic.

TABLE 18

The no. of oocytes obtained for IVM, maturation rate, fertilization rate, cleavage rate and pregnancy rate in experiment 1.

| | No Patients | oocytes for IVM no | MFII no (% MF-II) | 2PN fertilization no (% M II) | Cleavage no (% M II) | transfer no embryos | cryo-pres. cycles no | clinical preg. no | implantations |
|---|---|---|---|---|---|---|---|---|---|
| no FSH 36 h IVM | 10 | 37 | 28 (76) | 23 (62) | 20 (54) | 16 | 9 | 2 | 3 | 3 |
| + FSH 36 h IVM | 10 | 40 | 34 (85) | 26 (65) | 25 (62) | 17 | 9 | 5 | 2 | 2 |

TABLE 19

The hormone levels on day 3, day 6–7 and the day of aspiration in the two groups in experiment 1.

| | Group I no stimulation | Group II rec-FSH stimulation |
|---|---|---|
| no cycles | 10 | 10 |
| day of aspiration median (range) | 10 (8–12) | 9 (8–11) |
| serum FSH IU/ml medium (range) | | |
| day 3 | 6.6 (4.5–12.7) | 7.3 (5.1–10.9) |
| day 6–7 | 4.6 (3.7–10.0) | 7.3 (5.4–15.8) |
| day of aspiration | 7.3 (5.1–10.9) | 4.6 (3.7–10.0) |
| serum oestradiol nmol/l medium (range) | | |
| day 3 | 0.12 (0.07–0.44) | 0.15 (0.07–0.25)[b] |
| day 6–7 | 0.17 (0.11–0.47)[a,b] | 0.33 (0.17–3.7)[a,b] |
| day of aspiration | 0.47 (0.12–1.20)[b] | 0.32 (0.13–1.08) |
| serum LH IU/ml medium (range) | | |
| day 3 | 5.6 (2.4–11.6) | 6.1 (3.2–10.9) |
| day 6–7 | 8.7 (5.0–10.2) | 3.1 (0.9–8.3) |
| day of aspiration | 6.9 (4.2–11.8) | 6.1 (3.6–12.2) |
| serum inhibin-A medium (range) | | |
| day 3 | 9 (8–26) | 8 (<7–17)[b] |
| day 6–7 | 17 (7–29)[a,b] | 45 (16–89)[a,b,c] |

TABLE 19-continued

The hormone levels on day 3, day 6–7 and the day of aspiration in the two groups in experiment 1.

| | Group I no stimulation | Group II rec-FSH stimulation |
|---|---|---|
| day of aspiration serum inhibin-B medium (range) | 24 (12–52)[b] | 18 (<7–60)[c] |
| day 3 | 105 (<20–205)[b] | 153 (82–174)[b] |
| day 6–7 | 119 (66–327)[a,b] | 449 (143–2693)[a,b,c] |
| day of aspiration | 121 (81–175) | 107 (66–365)[c] |

[a]$p<0.05$,
[b]$p<0.05$,
[c]$p<0.05$.

TABLE 20

The number of oocytes obtained for IVM, the maturation and cleavage rates in low dose versus high dose gonadotrophin stimulation in experiment 2

| | Patients no | ampoules no median (range) | day of aspiration median (range) | size of the follicles median (range) | oestradiol day of aspiration median range | no oocytes | M II no (%) | cleavage | transfer no embryos | pregnant |
|---|---|---|---|---|---|---|---|---|---|---|
| low dose rec-FSH 48 h IVM | 5 | 6 | 9 8–11 | 10 7–15 | 0.3 0.05–1.89 | 21 | 15 (71%) | 10 (66%) | 7 | 1 |
| high dose rec-FSH 48 h IVM | 7 | 9 6–12 | 10 9–12 | 14 10–16 | 1.56 1.53–5.19 | 17 | 12 (71%) | 10 (83%) | 8 | |

What is claimed is:

1. A method of assaying for the presence or quantity of a substance in a sample from a mammal to determine whether non-fertilizable prophase ova capable of in vitro maturation and subsequent fertilization are present in the mammal and to select said ova for in vitro maturation and subsequent fertilization, the method comprising:
   obtaining a sample from a female mammal at various times during the menstrual cycle;
   testing the sample to determine the presence and relative concentration of at least one substance selected from the group consisting of a hormone, a small peptide hormone, a peptide hormone, a lipid, a nucleic acid, an intra- or intercellular messenger, and an enzyme;
   correlating the relative concentration of at least one substance with a reference level to determine if non-fertilizable prophase ova capable of in vitro maturation and fertilization are present; and
   subsequently retrieving ova from said mammal.

2. The method according to claim 1, wherein the identification of non-fertilizable prophase ova capable of in vitro maturation and the subsequent fertilization, cleavage and implantation of said ova in a mammal results in a pregnancy rate of at least 15%.

3. The method according to claim 1, wherein the sample is selected from the group consisting of body secrete, body fluid, cellular nutrients, follicle content, sputum, blood, urine, feces, uterine or vaginal secretes and components, menstruation products, epithelia and epithelia derived components, skin components, and dead or living cells.

4. The method according to claim 3, wherein the sample is a blood sample.

5. The method according to claim 1, wherein the mammal is a primate.

6. The method according to claim 5, wherein the primate is a human being.

7. The method according to claim 1, wherein the presence or quantity is determined by an immunoassay and/or a PCR reaction.

8. The method according to claim 1, wherein the substance is Inhibin A.

9. The method according to claim 1, wherein the substance is Estradiol.

10. A method for determining the timing of when non-fertilizable ova capable of in vitro maturation and subsequent fertilization are present in a mammal and retrieving said ova for in vitro maturation and subsequent fertilization, the method comprising:
    obtaining a sample from a female mammal;
    contacting the sample with at least one appropriate reagent for determining the presence and level of at least one marker substance selected from the group consisting of a hormone, a small peptide hormone, a peptide hormone, a lipid, a nucleic acid, an intra- or intercellular messenger, and an enzyme;
    detecting the presence and level of the at least one marker substance,
    correlating the level of said at least one marker substance with a reference level to determine if non-fertilizable prophase ova capable of in vitro maturation and fertilization are present; and
    subsequently retrieving ova from said mammal.

11. The method according to claim 10, wherein the sample from the mammal is a blood sample.

12. The method according to claim 10, wherein the mammal is a primate.

13. The method according to claim 12, wherein the primate is a human being.

14. The method according to claim 10, wherein timing is determined by a quantity of less than 10 pg/ml of the substance on day 3 in the menstrual cycle.

15. The method according to claim 14, wherein the substance is Inhibin A.

16. The method according to claim 10, wherein timing is determined by an increase in quantity of the substance of more than 80% from day 3 in the menstrual cycle to the day of aspiration.

17. The method according to claim 16, wherein the substance is Inhibin A.

18. The method according to claim 10, wherein timing is determined by an increase in the quantity of the substance of more than 87% from day 3 in the menstrual cycle to the day of aspiration.

19. The method according to claim 18, wherein the substance is Estradiol.

* * * * *